(12) United States Patent
Patterson et al.

(10) Patent No.: US 10,933,148 B1
(45) Date of Patent: Mar. 2, 2021

(54) SANITIZING DOWNLIGHT FIXTURE

(71) Applicant: Insight Lighting, Inc., Rio Rancho, NM (US)

(72) Inventors: Jaxon Patterson, Rio Rancho, NM (US); Geoffry Patterson, Rio Rancho, NM (US); Chris Kreuter, Rio Rancho, NM (US)

(73) Assignee: INSIGHT LIGHTING, INC., Rio Rancho, NM (US)

( * ) Notice: Subject to any disclaimer, the term of this patent is extended or adjusted under 35 U.S.C. 154(b) by 0 days.

(21) Appl. No.: 16/905,087

(22) Filed: Jun. 18, 2020

Related U.S. Application Data

(60) Provisional application No. 63/021,341, filed on May 7, 2020.

(51) Int. Cl.
| | |
|---|---|
| *F21V 21/00* | (2006.01) |
| *A61L 2/10* | (2006.01) |
| *F21V 23/04* | (2006.01) |
| *F21V 19/00* | (2006.01) |
| *F21S 8/02* | (2006.01) |
| *A61L 2/26* | (2006.01) |
| *F21V 21/03* | (2006.01) |
| *F21Y 115/10* | (2016.01) |
| *F21Y 113/13* | (2016.01) |

(52) U.S. Cl.
CPC .................. *A61L 2/10* (2013.01); *A61L 2/26* (2013.01); *F21S 8/026* (2013.01); *F21V 19/001* (2013.01); *F21V 21/03* (2013.01); *F21V 23/04* (2013.01); *A61L 2202/11* (2013.01); *F21Y 2113/13* (2016.08); *F21Y 2115/10* (2016.08)

(58) Field of Classification Search
CPC .......... A61L 2/10; A61L 2/26; A61L 2202/10; F21S 8/026; F21V 19/001; F21V 21/03; F21V 23/04; F21Y 2113/13; F21Y 2113/10
USPC ........................................................ 362/231
See application file for complete search history.

(56) References Cited

U.S. PATENT DOCUMENTS

| | | | |
|---|---|---|---|
| 9,700,641 B2 * | 7/2017 | Hawkins | ................. A61L 2/084 |
| 2007/0053188 A1 * | 3/2007 | New | ...................... B64D 13/00 362/276 |
| 2016/0030609 A1 * | 2/2016 | Peterson | .............. A01K 1/0047 362/84 |
| 2016/0136312 A1 * | 5/2016 | Park | .................... F21V 33/0044 362/231 |
| 2019/0254143 A1 * | 8/2019 | Hallack | ................... F21V 21/28 |

* cited by examiner

*Primary Examiner* — Laura K Tso
(74) *Attorney, Agent, or Firm* — Rod D. Baker

(57) ABSTRACT

A down-light fixture including both white-light-emitting diodes (LEDs) and antimicrobial ultraviolet (UV-C) LEDs. The white LEDs are arranged in the fixture so as to illuminate surfaces, e.g., items in a room of a building, when actuated. The UV-C LEDs also are arranged in the fixture so as to disinfect or sterilize the surfaces/items in the same room. The illumination LEDs and the disinfection LEDs are independently switchable "on" and "off," such that a user can controllably illuminate surfaces and/or objects, or disinfect surfaces and/or objects, or both illuminate and disinfect.

8 Claims, 3 Drawing Sheets

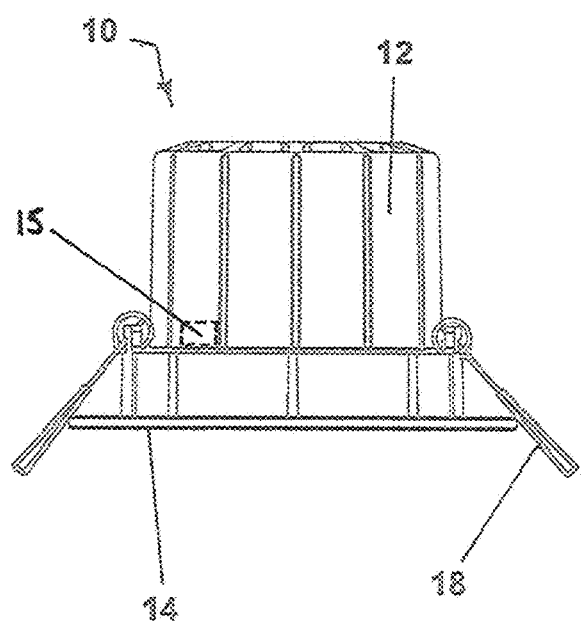
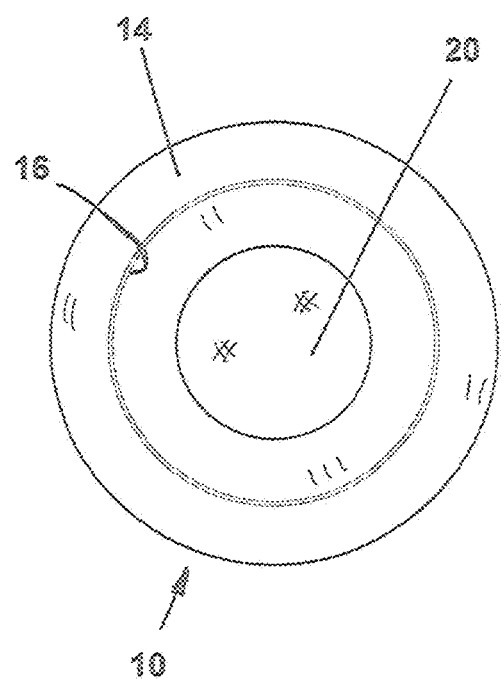

SANITIZING DOWNLIGHT FIXTURE

CROSS REFERENCE TO RELATED APPLICATIONS

This application claims priority to and the benefit of the filing of U.S. Provisional Patent Application Ser. No. 63/021,341, entitled "Sanitizing Downlight Fixture" filed 7 May 2020, the entire disclosure of which is incorporated herein by reference.

BACKGROUND OF THE INVENTION

Field of the Invention

This invention relates to light fixtures, particularly to a down-light fixture using incorporated light-emitting diodes, and specifically to a downlight fixture capable of either illuminating or disinfecting a surface, or both.

Background

It is known that ultraviolet light in the UV-C spectrum, directed to a surface for a period of time, can sterilize or disinfect the surface. There is an unmet need for a down-light fixture that is capable of not only disinfecting a surface with UV-C wavelength light, but which also or alternatively is capable of illuminating the same surface with white LED light.

SUMMARY OF THE INVENTION

There is disclosed a down light fixture of generally conventional physical structure, but distinguished in that it includes both white-light-emitting diodes (LEDs) and UV-C LEDs. The white LEDs are arranged in the fixture so as to illuminate surfaces, e.g., items in a room of a building, when actuated. The UV-C LEDs also are arranged in the fixture so as to disinfect or sterilize the surfaces/items in the same room. The illumination LEDs and the disinfection LEDs are independently switchable "on" and "off," so that a user can controllably illuminate surfaces and/or objects, or disinfect surfaces and/or objects, or both.

BRIEF DESCRIPTION OF THE DRAWINGS

The attached drawings, which form part of this disclosure, are as follows:

FIG. 2 is a side view of a down light fixture according to the present disclosure;

FIG. 3 is a bottom view of a down light fixture according to the present disclosure.

Like elements are labeled with like numerals in the several views; the drawings are not necessarily to scale, within a view or relative to each other.

DETAILED DESCRIPTION OF THE INVENTION

This invention relates to light fixtures, particularly a light fixture useable for illuminating an area or disinfecting an area, or for both illumination and disinfection. The light fixture is in a preferred embodiment a "down light" type of light fixture suitable for use in residential, commercial, or industrial buildings, and particularly in special rooms in such structures where control of disease-causing microorganisms is desired. A fixture according to the present system is adapted for installation in the ceiling of a room, or may be employed in some other overhead context, so to cast light rays downward for illuminating a room and its contents. The present system and apparatus include light-emitting diodes (LEDs) to provide beneficial light for illumination purposes. The light fixture apparatus also employs LEDs to emit sterilizing ultraviolet light to promote disinfection of surfaces and contents of a room in which the fixture is installed. It is to be understood that while a single fixture apparatus is described herein, a plurality of fixtures may be installed in a room, connected to an electrical power source by means of wired circuits and switches in compliance with known codes and conventions. It is desirable in selected contexts to be able to disinfect a room and its contents against the presence of microbes, particularly disease-causing pathogens. Pathogens of concern may include but are not necessarily limited to bacteria, viruses, protozoa or fungi. A fixture according to the present disclosure includes light-emitting diodes which emit ultraviolet (UV) light in germicidal wavelengths. UV irradiation is a disinfection method that uses short-wavelength ultraviolet ("ultraviolet C" or UV-C) light to kill or inactivate microorganisms by destroying their nucleic acids, and/or disturbing or disrupting their DNA. A fixture according to the present disclosure accordingly includes LEDs that emit UV-C light. The wavelength of germicidal UV-C is in the range of approximately 100 nanometer (nm) to approximately 280 nm, which wavelengths manifest effective sterilization power. It is known that UV-C exhibits highest germicidal effectiveness at a wavelength of 260 nm±10 nm, which is most effective to kill harmful microorganisms on surfaces in a room. In the present apparatus, therefore, UV-C LEDs are used that emit UV irradiation in wavelength(s) between 100 nm and 280 nm, preferably 260 nm±10 nm.

Figure 1:
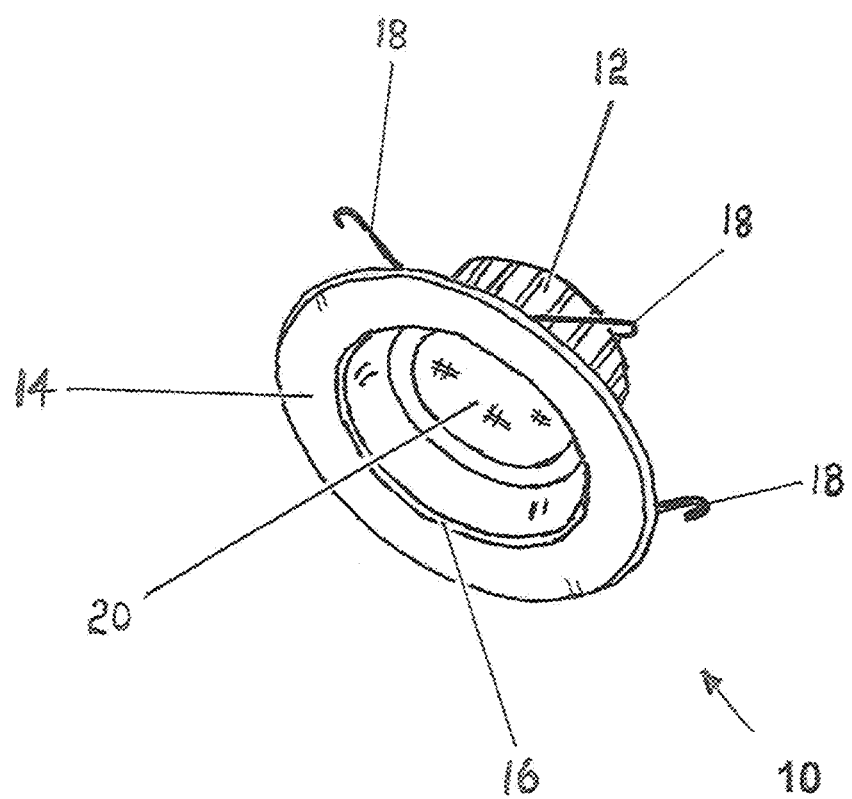
FIG. 1 is a perspective view of a down light fixture according to the present disclosure.

Attention is invited to FIGS. 1-3, showing a down light fixture 10 according to the present disclosure. One or more down light fixture 10 apparatuses can be installed and operated in a particular working area, such as in a room of a building. The room may be a room specially dedicated for uses requiring periodic sterilization or disinfection of room contents. The fixture 10 has a housing 12 and other non-electrical, structural, features of compositions and arrangements known in the art. The housing 12 is configured in size and shape to contain and position the electrical and optical components of the light fixture, including circuit components and light sources. Electrical power (ordinarily alternating current (AC)) is delivered to the interior of the housing 12 by any known or conventional wiring circuitry. Power may be delivered to the building from a public or private electrical grid according to convention.

The LED down light fixture 10 has UV-C LEDs and white light LEDs in the same fixture. The white LEDs are for standard lighting, while the UV-C LEDs are for sanitization or disinfecting purposes. The fixture 10 can selectively output only white light, only UV-C light, or a combination of both types of light. The fixture 10 can be powered via POE (power over ethernet) or with standard line voltage 120-347 v. The fixture has up to 30 w of white LED and 30 w of UV-C LED, for use in any size downlight 10.

As seen in FIGS. 1-3, the present fixture 10 may incorporate a bottom flange 14 in connection with the housing 12 for an aesthetic flush mount against a ceiling panel or drywall (not shown, but well-known). The flange 14 defines or surrounds peripherally a light aperture 16 through which the light rays emanating from within the housing 12 pass, for projection toward the areas and spaces to be illuminated. A clear or translucent/diffusing panel (not shown, but well-known), e.g. of glass or plastic, typically is provided at/in the aperture 16 to enclose the bottom of the housing 12 and, if desired, to diffuse or otherwise modify the light leaving the fixture 10. An optical lens (not shown, but also known in the art) optionally may be provided in or on the housing 12, e.g. between the aperture 16 and in the preferred embodiment a printed circuit board assembly (PCBA) 20 in which the LEDs of the apparatus are situated.

As best seen in FIG. 1, the PCBA 20 is situated within the housing 12 in a parallel confronting relationship with the aperture 16. The PCBA 20 is the "board" that results after completing printing solder paste on a printed circuit board, and after the mounting of various electronic components such as diodes, resistors, integrated circuits, capacitors, and any other components, such as transformers (depending on the application and desired characteristics of the board). Mounting means 18 or other attachment components may be provided for hanging/installing the fixture 10 in proper place in/on a room ceiling or other overhead structural item.

Figure 4:
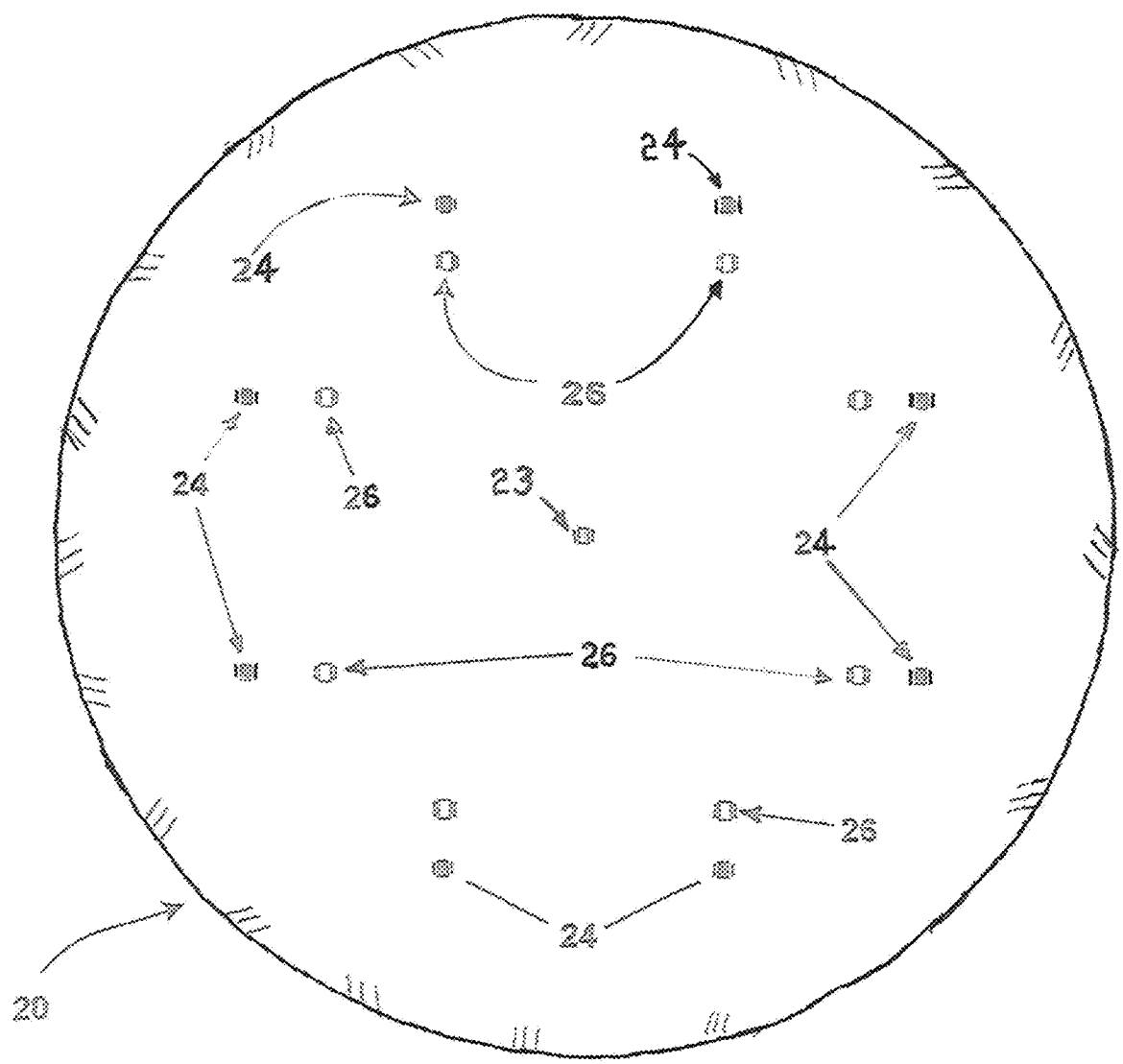
FIG. 4 is an enlarged bottom view of a printed circuit board assembly according to the present invention, useable in a fixture according to FIGS. 1-3.

Reference is made to FIG. 4, illustrating the side of a PCBA 20, according to a preferred embodiment of the present system and apparatus, from which visually illuminating light and disinfecting light is emitted. The PCBA 20 has arrayed thereon a plurality of illumination LEDs 24 and a plurality of disinfection LEDs 26. The illumination LEDs 24 preferably emit white light, of any correlated color temperature (CCT) suitable for standard illumination purposes, and of any appropriate wattage; illumination LEDs 24 are commercially available from a variety of manufacturers. The disinfection LEDs 26 also can be from any manufacturer, and of any suitable wattage, but rather than illuminating visible light they emit UV-C in a wavelength between 100 nm and 280 nm, preferably approximately 260 nm.

As seen in FIG. 4, the illumination LEDs 24 and disinfection LEDs 26 preferably are arranged on the PCBA 20 so as to cast dispersed and uniform illumination rays and disinfecting rays from the fixture 10 toward the surfaces to be lighted and/or sanitized. In a preferred embodiment of FIG. 4, a single unpaired central illumination LED 23 is located at or near the center of the PCBA 20, and thus is aligned with the center of the light aperture 16, so as to emit unimpeded illumination outward/downward from the fixture. Optionally, the central illumination LED 23 is of higher lumens than other illumination LEDs 24. The remaining illumination LEDs 24 and disinfection LEDs 26 preferably, but not necessarily, are arranged in pairs, each pair having one illumination LED 24 associated with one disinfection LED 26, so to promote even and uniform illumination and disinfection functions. Eight pairs of LEDs, each pair including an illumination LED 24 associated with a disinfection LED 26, are arranged peripherally around the central illumination LED 23. In the exemplary embodiment of FIG. 4, and analogizing the PCBA 20 to a metaphorical analog clockface, associated pairs of disinfection LEDs 26 and illumination LEDs 24 are located at about one o'clock, about two o'clock, about four o'clock, about five o'clock, about seven o'clock, about eight o'clock, about ten o'clock, and about eleven o'clock, respectively. The array of LEDs 24, 26 seen in FIG. 4 provides for simplified fabrication of the complete PCBA 20, and offers pleasant illumination of surfaces of interest as well as correspondingly effective disinfection of the same surfaces. Other embodiments of the present light fixture apparatus may use unpaired disinfection LEDs 26 and illumination LEDs 24. Other alternative embodiments also may employ a greater, or lesser, number of illumination LEDs 24 and disinfection LEDs 26 than the numbers seen in FIG. 4. The number and locations of LEDs 24, 26 may be selectively adapted to accommodate the needs and circumstances of a particular context or application. The numbers of either type of LED 24 or 26, and the manner in which they are arranged, are chosen to satisfy the specifications for the room or other space in which the fixture(s) 10 are used.

There is provided in operative connection with the fixture 10 and/or its corresponding PCBA 20, a circuit switching means 15 (FIG. 2) known in the art whereby the illumination LEDs 24 and disinfection LEDs 26 are able to be turned on or off independently. Thus, when it is desired only to illuminate objects in a room, an appropriate remotely operated manual switch (e.g. on a wall in the room) is actuated to activate only the illumination LEDs 24 in the room (while leaving the disinfection LEDs 26 off). Alternatively, if it is desired only to disinfect objects in the room, an appropriate switch (e.g. on a wall in the room) is actuated to activate only the disinfection LEDs 26 (while leaving the illumination LEDs 24 "off" and dark). Yet further, if and when it is desired to both illuminate and disinfect surfaces in the room, the respective switch(es) are operated to activate and "turn on" the illumination LEDs 24 and the disinfection LEDs 26. Of course, the switches also can be operated to turn "off" all the LEDs 24, 26 in a room or other working area. Thus, a switch may be a multi-position rotary or rocker switch to permit a user to select between having no LEDs tuned on, all LEDs on, only disinfection LEDs turned on, or only illumination LEDs turned on.

Although the invention has been described in detail with particular reference to these preferred embodiments, other embodiments can achieve the same results. In this description, specific details are set forth, such as specific materials, structures, processes, etc., in order to provide a thorough understanding of the present invention. However, as one having ordinary skill in the art of light fixture construction would recognize, the present invention can be practiced without resorting strictly only to the details specifically set forth. In other instances, well-known concepts and compositions have not been described in detail, in order not to unnecessarily obscure the present invention.

Only some embodiments of the invention and but a few examples of its versatility are described in the present disclosure. It is understood that the invention is capable of use in various other combinations and is capable of changes or modifications within the scope of the inventive concept as expressed herein. Modifications of the invention will be obvious to those skilled in the art and it is intended to cover with the appended claims all such modifications and equivalents.

What is claimed is:
1. A sanitizing light fixture apparatus comprising:
 a downlight comprising:
  a housing for containing electrical and optical components;
  a printed circuit board assembly in the housing;
  a plurality of illumination light emitting diodes arrayed on the printed circuit board,
  a plurality of disinfection light emitting diodes arrayed on the printed circuit board;
  a light aperture through which pass light rays emanating from within the housing; and at least one switch for turning on or off the plurality of illumination light emitting diodes and the plurality of disinfection light emitting diodes independently of each other;

wherein the fixture is operable to emit only disinfecting light, or only visually illuminating light, or both disinfecting and visually illuminating light.

2. The apparatus according to claim 1 wherein the plurality of illumination light emitting diodes includes a single central illumination LED aligned with a center of the light aperture.

3. The apparatus according to claim 1 wherein the plurality of illumination light emitting diodes and the plurality of disinfection light emitting diodes are arranged in pairs, each pair disposed on a lower side of the printed circuit board assembly and comprising one illumination LED associated with one disinfection LED.

4. The apparatus according to claim 1 wherein the plurality of disinfection light emitting diodes comprise diodes emitting UV C light of a wavelength between approximately 100 nanometer (nm) and approximately 280 nm.

5. A sanitizing light fixture apparatus comprising:
a down light comprising:
a housing for containing electrical and optical components;
a bottom flange connected to the housing and mountable against a ceiling panel,
a printed circuit board assembly in the housing;
a plurality of illumination light emitting diodes arrayed on the printed circuit board;
a plurality of disinfection light emitting diodes arrayed on the printed circuit board;
a light aperture through which pass light rays emanating from within the housing; and
at least one switch for turning on or off the plurality of illumination light emitting diodes and the plurality of disinfection light emitting diodes independently of each other;
wherein the fixture is operable to emit only disinfecting light, or only visually illuminating light, or both disinfecting and visually illuminating light; and wherein the plurality of illumination light emitting diodes and the plurality of disinfection light emitting diodes are arranged in pairs, each pair disposed on a lower side of the circuit board assembly and comprising one illumination LED associated with one disinfection LED.

6. The apparatus according to claim 5 wherein the plurality of illumination light emitting diodes includes a single central illumination LED aligned with a center of the light aperture.

7. A sanitizing light fixture apparatus comprising:
a downlight comprising:
a housing for containing electrical and optical components;
a bottom flange connected to the housing and mountable against a ceiling panel;
a light aperture, defined by the bottom flange, through which pass light rays emanating from within the housing;
a printed circuit board assembly in the housing;
single central illumination LED aligned with a center of the light aperture,
a plurality of illumination light emitting diodes arrayed radially around the central illumination LED on the printed circuit board;
a plurality of disinfection light emitting diodes arrayed radially around the central illumination LED on the printed circuit board; and
at least one switch for turning on or off the plurality of illumination light emitting diodes and the plurality of disinfection light emitting diodes independently of each other,
wherein the fixture is operable to emit only disinfecting light, or only visually illuminating light, or both disinfecting and visually illuminating light.

8. The apparatus according to claim 7 wherein the plurality of illumination light emitting diodes and the plurality of disinfection light emitting diodes are arranged in pairs, each pair disposed on a lower side of the printed circuit board assembly and comprising one illumination LED associated with one disinfection LED.

* * * * *